United States Patent [19]

Alfano

[11] E Patent Number: Re. 31,815

[45] Reissued Date of Patent: Jan. 29, 1985

[54] METHOD AND APPARATUS FOR DETECTING THE PRESENCE OF CARIES IN TEETH USING VISIBLE LUMINESCENCE

[75] Inventor: Robert R. Alfano, Bronx, N.Y.

[73] Assignee: Philips Medical Systems, Inc., Shelton, Conn.

[21] Appl. No.: 381,170

[22] Filed: May 24, 1982

Related U.S. Patent Documents

Reissue of:

[64] Patent No.: 4,290,433
Issued: Sep. 22, 1981
Appl. No.: 67,771
Filed: Aug. 20, 1979

[51] Int. Cl.[3] ..... A61B 6/00

[52] U.S. Cl. ..... 128/665; 356/318; 356/237

[58] Field of Search ..... 128/633-634, 128/665-666, 4-6, 15-16, 23, 777; 433/25, 255, 229; 358/98; 356/316-319, 237, 239

[56] References Cited

U.S. PATENT DOCUMENTS

| | | | |
|---|---|---|---|
| 3,051,166 | 8/1962 | Hornanian | 358/98 |
| 3,709,612 | 1/1973 | Clemens | 128/633 |
| 3,811,777 | 5/1974 | Chance | 356/318 |
| 4,170,987 | 10/1979 | Anselmo et al. | 128/665 |
| 4,178,917 | 12/1979 | Shapiro | 128/665 |

FOREIGN PATENT DOCUMENTS

| | | | |
|---|---|---|---|
| 2725793 | 1/1978 | Fed. Rep. of Germany | 128/23 |

*Primary Examiner*—Kyle L. Howell
*Assistant Examiner*—Francis J. Jaworski
*Attorney, Agent, or Firm*—Yuter, Rosen & Dainow

[57] ABSTRACT

A method and apparatus for detecting the presence of caries in human teeth using visible luminescence. A region to be examined is excited with a beam of monochromatic light. The intensity of the visible light emitted from the region is measured at two predetermined wavelengths, one where the intensity dependence of the spectra is about the same for caries and noncaries and the other where the relative intensity increases significantly in the presence of caries. A signal corresponding to the difference in the two intensities is obtained and then displayed. By first determining the magnitude of the difference signal at a nondecayed region, any increases in the magnitude as other regions are probed indicate the presence of caries. The invention is based on the discovery that the visible luminescence spectra for decayed and nondecayed regions of a human tooth are substantially different and that the differences are such that visible luminescence from teeth can be used to detect the presence of caries.

33 Claims, 8 Drawing Figures

METHOD AND APPARATUS FOR DETECTING THE PRESENCE OF CARIES IN TEETH USING VISIBLE LUMINESCENCE

Matter enclosed in heavy brackets [ ] appears in the original patent but forms no part of this reissue specification; matter printed in italics indicates the additions made by reissue.

BACKGROUND OF THE INVENTION

The present invention relates to a method and apparatus for detecting the presence of caries in teeth and more particularly, to a method and apparatus for detecting the presence of caries in the teeth of a person using visible luminescence.

Dental caries or tooth decay is a very common and well known type of disease which, if not properly treated, results in a breakdown of the hard structures of the teeth. The progress of tooth decay is gradual, starting slowly from the outside at the enamel and then progressing more rapidly in the dentin. It is believed that dental caries are caused primarily by the action of acid-producing bacteria on certain carbohydrates, principally sugar. If detected, dental decay can be treated by removing the decayed area and filling the resulting cavity with silver amalgam or other inert cavity material. If untreated, dental caries can cause the eventual destruction of the tooth as well as infection on abscess of the jawbone.

In the past, dental caries has been detected by two techniques, one by visual inspection and the other through the use of X-rays.

The problem with visual inspection is that it is not always possible to detect the presence of caries by simply looking at the teeth, especially if the caries is very small or in a very early stage or in an area where it cannot be easily seen. On the other hand, although X-rays have proven to be a very effective manner for detecting the presence of caries and other problems or disorders in the teeth and/or gums, the potentially harmful effects of subjecting people to X-ray radiation has become a matter of great concern over the last several years. In particular, the quantitive relationship between low-dose exposure to X-rays and possible harmful effects, such as cancer, is not clearly known.

In view of the possible dangerous effects of X-rays, it would appear that a definite need exists for a new technique for detecting the presence of caries and specifically for a technique which can either eliminate or substantially reduce the necessity of X-ray examinations.

Experiments have been conducted in the past which reveal that teeth luminesce when excited by light. In an article by R. L. Hartles and A. G. Leaver appearing in the 1954 Biochemistry Journal, pp. 632–638, the results of certain experiments performed to determine the luminescent properties of teeth when exposed to ultraviolet radiation are discussed at length. Other known articles dealing with the luminescent properties of teeth when exposed to ultraviolet radiation are an article by K. G. Hoerman and S. A. Mancewicz appearing in the 1964 Oral Biology Journal, Volume 9, pp. 517–534 and an article by K. G. Hoerman and S. A. Mancewicz appearing in the 1964 Oral Biology Journal, Volume 9, pp. 535–544.

In U.S. Pat. No. 2,437,916 to W. F. Greenwald there is described a technique for examining living tissue which involves illuminating the tissue with a beam of light and then measuring the intensity of the reflected light at certain wavelength ranges using a phototube and different colored filters.

In U.S. Pat. No. 3,674,008 to C. C. Johnson there is described an instrument which quantitatively measures optical density of a transilluminated body portion. The instrument comprises a controllable, relatively low-frequency oscillator generating pulses which are applied to a light source through a first expand and delay circuit. A light-conducting source to one side of the body portion and a similar means optically couples another side of the body portion to a light detector. Alternatively, the light source and detector may be placed directly on the body portion. After compensation for ambient light, the output of the detector is coupled to a sample and hold circuit which is triggered by the controllable oscillator through a second expand and delay circuit. The stored signal in the sample and hold circuit is proportional to transmittance and is converted to a visual indication of optical density by a calibrated display means. Methods of using the instrument in diagnosis are discussed, as are further applications to spectrophotometric determinations.

In U.S. Pat. No. 3,963,019 to R. S. Quandt there is described a method and apparatus for detecting changes in body chemistry, for example, glycemia, in which a beam of light is projected into and through the aqueous humor of the patient's eye. An analyzer positioned to detect the beam on its exit from the patient's eye compares the effect the aqueous humor has on said beam against a norm. An excess of deficiency of glucose present in the aqueous humor produces a corresponding positive or negative variation in the exiting beam and thereby indicates a hyper or hypo glycemia condition in the body chemistry of the patent being tested.

In U.S. Pat. No. 4,029,085 to D. P. DeWitt et al there is described a method for determining the bilirubin concentration in the blood serum of a person from measurement of the spectral reflectance of the skin. The disclosed method detects the severity of jaundice, a common neonatal condition, and enables determination of the type of treatment regimen and needed to prevent the bilirubin level from becoming sufficiently high to cause kernicterus which can result in brain damage. The method includes measuring the reflectance of the skin within a predetermined frequency spectrum, and more particularly, at a number of specific wavelengths in the visible portion of the spectrum.

In Medical and Biological engineering, Volume 6, No. 4; August 1968, pp. 409–413, there is described a technique for tissue identification during needle puncture by reflection spectrophotometry.

SUMMARY OF THE INVENTION

It is an object of this invention to provide a new and improved technique for detecting the presence of caries in teeth.

It is another object of the invention to provide a technique for detecting the presence of caries in the teeth which does not involve the use of X-rays.

It is still another object of this invention to provide a technique for detecting the presence of caries in teeth that does not involve the use of other potentially harmful radiation, such as ultraviolet radiation.

It is yet still another object of this invention to provide a technique for detecting the presence of caries in the teeth of a person which is reliable, inexpensive, and easy to use.

It is another object of this invention to provide a technique for detecting the presence of caries in teeth which does not require the use of X-ray sensitive plates or film.

It is still another object of this invention to provide a technique for detecting the presence of caries in teeth which is suitable for use with conventional photographic film and associated optical filters.

It is yet still another object of this invention to provide a technique for detecting the presence of caries in teeth using visible light as an exciting source and visible luminescence to probe for caries.

The present invention is based on the discovery that the [visiblee] *visible* luminescence spectra from caries and non-decayed regions of a tooth are substantially different, and in particular, that in certain regions of the visible spectrum the intensity of the luminescence for caries and nondecayed teeth is about the same while in other regions of the visible spectrum the relative intensity increases substantially in the presence of caries. The present invention is also based on the further discoveries that the emission from amalgam and metals is weaker than the emission from caries in the region where the emission increases in the presence of caries and that the relative intensity change of the spectrum from adaptic is less than the relative change for noncarious regions in the red portion of the spectrum. Finally, it has been discovered that the visible luminescence can be achieved using visible light as the excitation source.

The method for detecting the presence of caries according to the teachings of this invention and based on the above noted discoveries involves illuminating a region to be examined with a beam of monochromatic light, measuring the intensity of the visible luminescent radiation at a wavelength where the intensity dependence of the spectrum is about the same for caries and noncaries and at a wavelength where the intensity dependence of the spectrum increases a measurable amount in the presence of caries and then displaying a signal corresponding to the difference. By first determining the magnitude of the difference signal when a region known to be noncarious is illuminated, increases in the magnitude of the signal as other regions are examined will indicate the presence of caries.

The apparatus for detecting the presence of caries according to the teachings of this invention and based on the above noted discoveries includes means for illuminating a region to be examined with a beam of monochromatic light, means for measuring the intensity of the emitted light at two wavelengths, one where the intensity dependence of the spectrum is about the same for caries and noncaries and the other where the intensity dependence of the spectrum increases in the presence of caries, means for producing a signal corresponding to the difference in the two intensities and means for displaying the difference signal.

The foregoing and other objects and advantages will appear from the description to follow. In the description, reference is made to the accompanying drawing which forms a part thereof, and in which is shown by way of illustration a specific embodiment for practicing the invention. This embodiment will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

BRIEF DESCRIPTION OF THE DRAWINGS

The accompanying drawings illustrate a complete embodiment of the invention according to the best mode so far devised for the practical application of the principles thereof, and in which.

DETAILED DESCRIPTION

The present invention is directed to a method and apparatus for detecting the presence of caries in the teeth of a person using visible luminescence.

Figure 1:
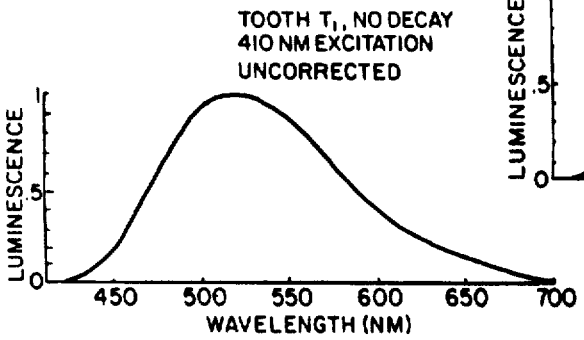
FIG. 1 is a graphical illustration of emission spectra measurements made on a known noncarious region of a human tooth excited with blue light at a wavelength of 410±5 mm.
Figure 2:
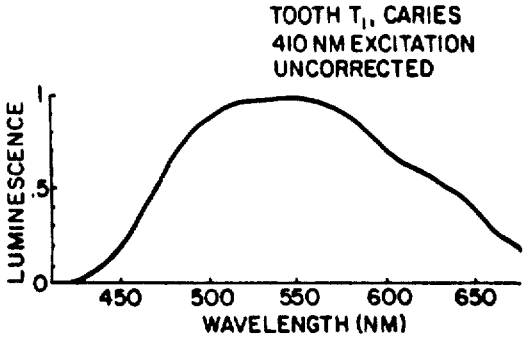
FIG. 2 is a graphical illustration of the emission spectra measurements made on the same tooth as in FIG. 1 with the same light but at a known carious region.

Referring now to the drawings, there is shown in FIG. 1 a graph of emission spectrum measurements made on an extracted human tooth $T_1$ excited by blue light at a wavelength of 410±5 nm on a region known to be noncarious and in FIG. 2 a graph of emission spectrum measurements made on the same tooth by the same light over a region known to have caries. Luminescent radiation from the tooth was collected into a SPEX ¼-meter scanning spectrometer blazed at 500 nm, second order. An RCA 7265 (S-20) photomultiplier located at the exit of the spectrometer measured the intensity at different wavelengths. The output of the photomultiplier was connected to a lock-in-recorder to display the spectrum. The emission spectra were uncorrected for the spectral response of the system. The intensities from both regions were comparable in magnitude, however, the spectra were normalized to unity at the intensity maximum. The emission spectra from the region containing caries (FIG. 2) contained no more that a 25% contribution from the surrounding region. The intensity variations of the teeth examined for caries and noncaries were typically in an order of magnitude of each other.

Figure 3:
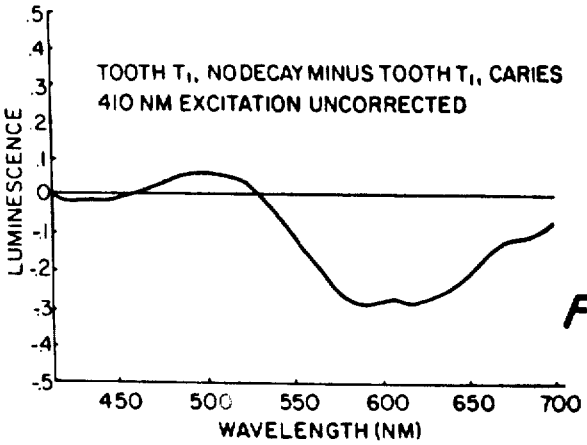
FIG. 3 is a graphical illustration of the difference of the spectra in FIG. 1 and the spectra in FIG. 2.

The difference spectra between the nondecayed and the decayed regions is illustrated in FIG. 3.

The salient features of the data displayed in FIGS. 1-3 are that the caries spectra are shifted to the red by about 200 Å and have more intensity in the longer wavelength region than the spectral obtained from a non-carious region. The largest difference between the spectra from caries and non-caries occurs in the region between 540 and 650 nm. with the largest difference occuring at 620 nm. On the other hand, in the region between around 450 and 500 nm. the difference is extremely small and about constant. Furthermore, when the spectrum for caries is divided by the spectrum for noncaries, the relative intensity change in the red portion of the spectrum (i.e. 540 to 650 nm) is about two to four times larger than the intensity change in the blue portion of the spectrum (i.e. 420 to 500 nm).

Figure 4:
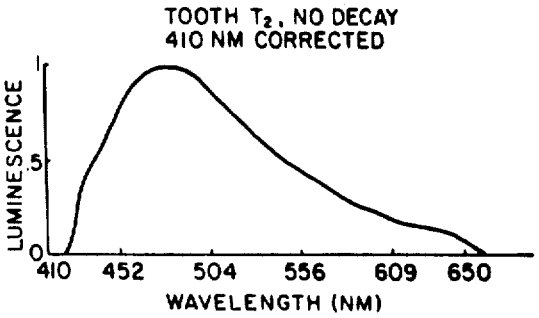
FIG. 4 and 5 are graphical illustrations similar to FIGS. 1 and 2 respectively but for a different tooth.
Figure 5:
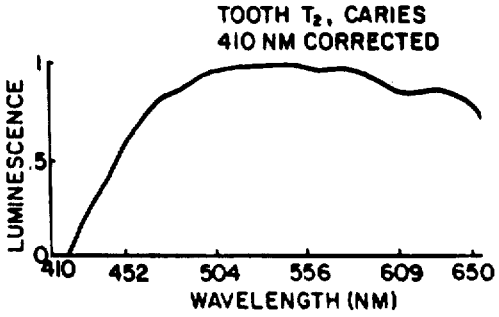

Graphs of the visible emission spectrum measurements for another tooth $T_2$ over a known noncarious region and a known carious region using the same equipment as above, but being corrected for the spectral response of the detection system are illustrated in FIGS. 4 and 5 respectively.

Figure 6:
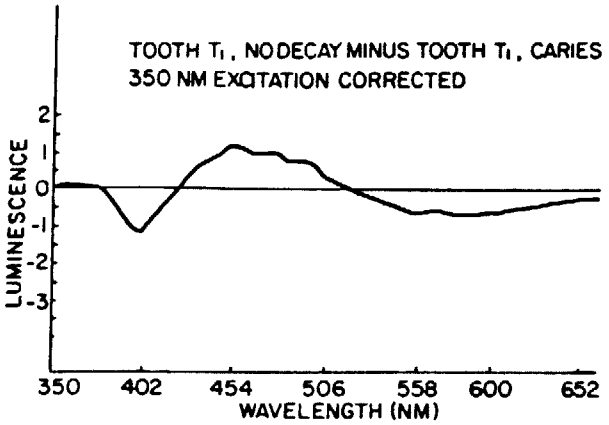
FIGS. 6 and 7 are graphical illustrations similar to FIG. 3 for the tooth used in FIGS. 1 and 4, respectively, but with a light source of 350 nm rather than 410 nm.
Figure 7:
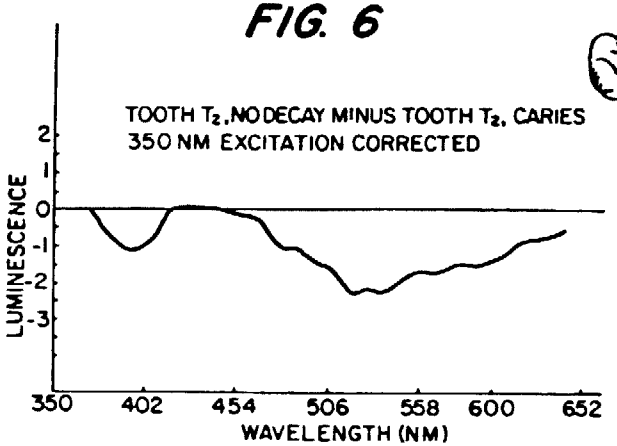

Graphs of the difference spectra for teeth $T_1$ and $T_2$ obtained using the same equipment as used to obtain the graphs in FIGS. 1-3, but with a light source of 350 nm. instead of 410 nm are illustrated in FIGS. 6 and 7 respectively.

As can be seen, in each case the intensity over a carious region is substantially greater than the intensity for a noncarious region in the red region of the spectrum and in each instance there is an area in the blue region of the spectrum where the difference in decayed and nondecayed regions is minimal.

Figure 8:
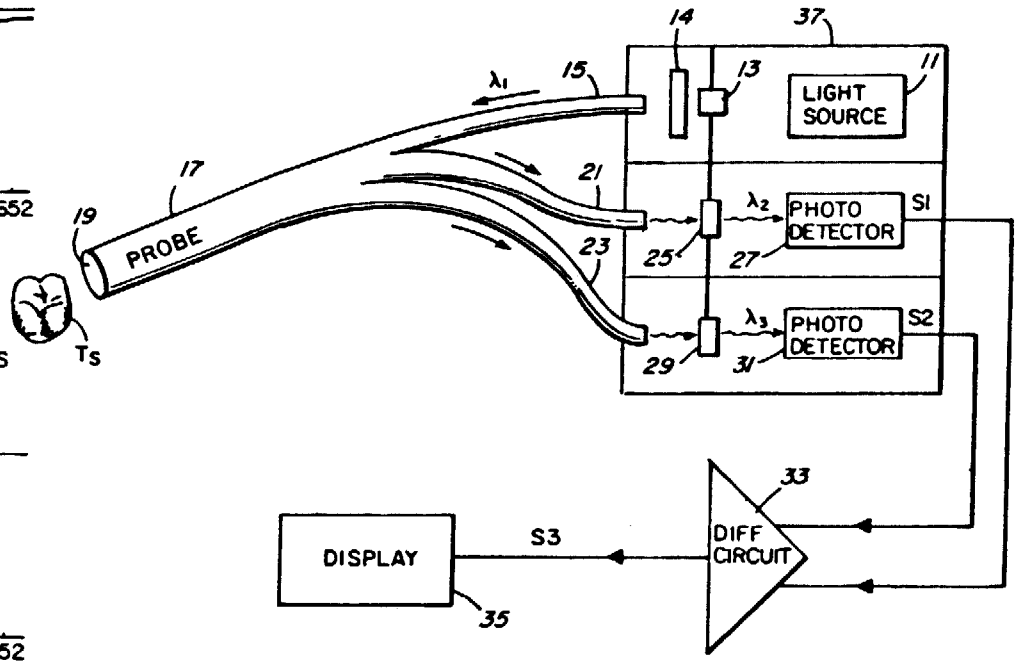
FIG. 8 is a simplified diagram of an embodiment of the apparatus of the invention.

Referring now to FIG. 8 there is illustrated an apparatus for detecting the presence of caries in the teeth of a person according to the teachings of this invention.

The apparatus includes a source 11 of white light, such as tungsten-halogen filament lamp, and a narrow band filter 13. Alternatively, source 11 may comprise a laser. Light source 11 has power coupled to it from a conventional power supply (not shown). Narrow band filter 13 has a bandwidth of less than about 30 nm and preferably less than about 10 nm and is designed to pass light at a wavelength $\lambda_1$.

Light from source 11 that is passed by filter 13 is passed through a chopper 14 which removes any ambient light present and is then fed into an input leg 15 of a fiber optic probe 17. The light entering fiber optic probe 17 emerges at the probing end 19 and impinges on a tooth $T_s$ enters probing end 19 and is conducted out of fiber optic probe 17 through output legs 21 and 25 which are located at the same end as input leg 15.

Fiber optic probe 17 is made up basically of a bundle of optical fibers. The diameter of the bundle is preferably about ½ to 3 nm. The fibers within the bundle are preferably randomly arranged to reduce any geometrical collection effects. Fiber optic probe 17 may include a lens or lens system (not shown) at the probing end 19 so that non-contact probing may be achieved, facilitating examination of areas between teeth or other areas not easily reachable by direct contact-probing.

Light emerging from output leg 21 is passed through a narrow band filter 25 having a bandwidth of less than about 10 nm and designed to pass light at a wavelength $\lambda_2$, in the visible spectrum where the intensity is constant for caries and noncaries, and impinges on a photodetector 27. Light emerging from output leg 23 is passed through a narrow band filter 29 having a bandwidth of less than about 10 nm and designed to pass light at a wavelength $\lambda_3$, in the visible spectrum [when] *where* the intensity increases in the presence of caries, and impinges on a photodetector 31.

The value of $\lambda_2$ depends, at least partially, on the value of $\lambda_1$. For example, if $\lambda_1$ is 410 nm, then $\lambda_2$ may be 450 nm. The value of $\lambda_3$ is also, at least partially, dependent on $\lambda_1$. Thus, if $\lambda_1$ is 410 nm then $\lambda_3$ may be around 610 nm. The value of $\lambda_1$ is any wavelength that will cause teeth to luminesce in the visible spectrum at a wavelength $\lambda_2$ where the intensity is constant for caries and noncaries and at a wavelength $\lambda_3$ where the intensity increases measurably in the presence of caries. Wavelength $\lambda_1$ is preferably in the visible rather than ultraviolet region to avoid the potential hazards of exposure to ultraviolet radiation. Photodetectors 27 and 31 are conventional photodetectors having maximum sensitivity in the regions of interest, namely at wavelengths $\lambda_2$ and $\lambda_3$ respectively.

Photodetectors 27 and 31 each produce an electrical signal output whose magnitude $S_1$ and $S_2$ respectively, is proportional to the intensity of the incident light. The electrical output signals from photodetectors 27 and 31 are each fed into an electronic circuit 33, such as a differential lock-in amplifier, which is turned to the frequency and phase of the chopper and which produces an electrical output signal whose magnitude $S_3$ is equal to the differences between the two output signals $S_1$ and $S_2$. Alternatively, electronic circuit 33 may be a differential amplifier tuned to the frequency of the chopper 14. Furthermore, chopper 14 may be eliminated, if the ambient light around the region being probed is not in the area of spectral interest.

The output of electronic circuit 33 is connected to a display 35 which may be in the form of a digital or analog meter or a light or buzzer which is activated when difference signal $S_3$ exceeds a predetermined threshold. Display 35 may be mounted directly on fiber optic probe 17.

[Lite] *Light* source 11, narrow hand filters 13, 25 and 29 and photodetectors 27 and 31 are all situated in a light-tight compartmented housing 37.

In detecting the presence of caries in accordance with the invention, the probe signals $S_1$ and $S_2$ are first determined for a known non-carious region. Any changes in the difference between signals $S_1$ and $S_2$ will indicate that caries are present.

In practice, the probe signals $S_1$ and $S_2$ received from a known nondecayed region are preferably balanced to zero (i.e. $S_1$–$S_2$ adjusted to zero) so that any increase in $S_2$ will produce an unbalanced condition or a voltage signal $S_3$ having a magnitude greater than zero. This allows the threshold value for an indicator light or buzzer to be zero. The signals $S_1$ and $S_2$ can be adjusted to zero by any known means such as by adjusting the base voltages of the photodetectors or adding the necessary circuitry to permit adjustment of electronic circuit 31.

Instead of taking the difference signals $S_1$ and $S_2$, the ratio of signals $S_1$ and $S_2$ may be used to determine the relative change of the spectra. This may be achieved using any conventional type of dividing circuit.

The relative magnitudes of probe signals $S_1$ and $S_2$ actually obtained from a nondecayed area of a human tooth, from amalagm, from adaptic and from a decayed portion of the same tooth when $\lambda_1$ is 410 nm, $\lambda_2$ is 460 nm and $\lambda_3$ is 600 nm, are shown in the following table. In the table, the probe signals $S_1$ and $S_2$ for the nondecayed region of the tooth were balanced at the same value by adjusting the base voltages of the photodetectors and the values of probe signals $S_1$ and $S_2$ for the amalagm, for the adaptic and for the decayed region are values obtained after such adjustments.

TABLE 1

| Tooth Non-Decayed Area | Amalagm | Adaptic | Tooth Decayed Area |
|---|---|---|---|
| [$S_2$]$S_1 \simeq 200$ MV | $S_1 \simeq 2$ MV | $S_1 \simeq 200$ MV | $S_1 \simeq 100$ MV |
| $S_2 = 200$ MV | $S_2 \simeq 1$ MV | $S_2 \simeq 190$ | $S_2 \neq 200$ MV |

TABLE 1-continued

| Tooth Non-Decayed Area | Amalagm | Adaptic | Tooth Decayed Area |
|---|---|---|---|
| | | MV | |

As can be seen, once the probe signal $S_1$ and $S_2$ are balanced at a nondecayed area, the difference between $S_1$ and $S_2$ (i.e. $S_1-S_2$) is about 1 MV for amalagm, about +10 MV for adaptic and about −100 MV for a decayed area. Thus, a decayed area can be clearly distinguished from a nondecayed area, from amalagm and from adaptic. It has been found that with a balance accuracy of 1%, caries of about 100 microns can be separated from nondecayed regions with a signal to noise ratio of greater than one. It has also been found that caries 0.01 $cm^2$ in size between teeth can be detected from the scattered light of a 1 $cm^2$ surface.

In another embodiment of the invention, the presence of caries can be detected by exciting a region of the teeth to be examined with a beam of substantially monochromatic light, forming an image of the light emitted from the region at a wavelength where the intensity [increases] *decreases* in the presence of caries and then recording the image on a suitable recording medium.

As can be appreciated, the invention does not involve the use of X-ray radiation and does not require the use of radiation sensitive plates. Furthermore, since the indication of caries is based on the difference between signals $S_1$ and $S_2$ and not merely the intensity of signal $S_2$, any changes in the light emitted from a region under test, such as may be caused by increasing or decreasing the distance from the probe to the region under test, will not produce a change in the difference. Also, since the excitation radiation is visible light, the tooth or region thereof being illuminated can be readily observed.

What is claimed is:

1. A method for detecting the presence of caries in the teeth of a person comprising:

(a) exciting a region of the teeth to be examined with a beam of light that is at least substantially monochromatic, (b) measuring the intensity of the visible luminescence emitted from the region at two predetermined wavelengths, one where the relative intensity dependence of the spectra is about the same for caries and non-decayed regions and the other where the intensity [increases] *changes* measurably in the presence of caries, and (c) determining if caries is present in accordance with said measurements.

2. The method of claim 1 and wherein determining if caries is present comprises determining the difference in intensities at the two wavelengths in a noncarious region and then detecting increases in the difference as other regions are excited.

3. The method of claim 1 and wherein determining if caries is present includes producing a signal corresponding to the difference between the intensitites at the two wavelengths and then displaying said signal.

4. The method of claim 1 and wherein determining if caries is present comprises producing a signal proportional to the difference between the intensity at the wavelength where the relative intensity dependence of the spectrum is about the same for caries and noncaries and the intensity at the wavelength where the intensities increase in the presence of caries.

5. The method of claim 4 and wherein the beam of light is visible light and has a bandwidth of about no more than 30 nm.

6. The method of claim 5 and wherein the visible light is between about 400 nm and 700 nm.

7. The method of claim 6 and wherein one of said wavelengths at which the intensity is measured is between 440 and 470 nm and the other wavelength at which the intensity is measured is between 560 and 640 nm.

8. The method of claim 1 and wherein determining if caries is present comprises determining the ratio of the intensities at the two wavelengths in a noncarious region and then detecting increases in the ratio as other regions are excited.

9. The method of claim 1 and wherein the beam of exciting light has a wavelength between 350 and 600 nm.

10. A method for detecting the presence of caries in the teeth of a person comprising:

(a) exciting a region of the teeth to be examined with a beam of monochromatic light at a wavelength $\lambda_1$, (b) measuring the intensity of the visible luminescence emitted from the region at a wavelength $\lambda_2$ and at a wavelength $\lambda_3$, (c) producing a signal corresponding to the intensity at wavelength $\lambda_3$ less the intensity at wavelength $\lambda_2$, (d) displaying said signal, and (e) determining if caries is present in accordance with said signal, wherein $\lambda_2$ is a wavelength where the relative intensity dependence of the spectra is about the same for caries and noncaries, $\lambda_3$ is a wavelength where the intensity increases in the presence of caries and $\lambda_1$ is a wavelength that will produce emission from teeth at $\lambda_2$ and $\lambda_3$.

11. A method for detecting the presence of caries in the teeth of a person comprising:

(a) exciting a known noncarious region of the teeth with a beam of monochromatic light, (b) measuring the intensity of the emission at a wavelength where the relative intesity dependence of the spectra is about the same for caries and noncaries and at a wavelength where the intensity increases in the presence of caries, (c) displaying a signal corresponding to the differences in the two intensities, and then (d) detecting increases in said signal as other regions of the teeth are excited.

12. A method for detecting the presence of caries in a region of teeth of a person comprising:

(a) exciting the region with light, (b) measuring the intensity of the visible luminesce from the region at a wavelength where the relative intensity dependence of the spectra is about the same for caries and non-caries and at a wavelength where the intensity increases in the presence of caries; and (c) determining if caries is present on the basis of the difference in intensities at the two wavelengths.

13. Apparatus for use in detecting the presence of caries in the teeth of a person comprising:

(a) means for illuminating a region to be examined with a beam of monochromatic light, the wavelength of the beam of monochromatic light being one which will produce emission from the region at a wavelength where the intensity is about the same for caries and non caries and at a wavelength where the intensity increases in the presence of caries, (b) means for measuring the intensity of the light emitted from said region on illumination by said illuminating means at a wavelength where the relative intensity dependence of the spectra is about the same for caries and noncaries and at a wavelength where the intensity increases in the presence of caries and producing an electrical signal whose output corresponds to the intensity at each wavelength, (c) means producing an electrical signal corresponding to the difference in said two electrical signals, and (d) means for displaying said difference electrical signal.

14. Apparatus for detecting the presence of caries in the teeth of a person comprising:

(a) a source of visble monochromatic light for illuminating a region at a wavelength which will produce emission at a wavelength where the intensity is about the same for caries and noncaries and at a wavelength where the intensity changes in the presence of caries.

(b) a pair of photodetector means for measuring the intensity of light emitted from said region at two different wavelengths, one of said wavelengths being a wavelength where the intensity is about the same for caries and noncaries and the other wavelength being a wavelength where the intensity changes in the presence of caries, both of said wavelengths being different from the wavelength of the source, (c) means for directing light to said region from the source and transmitting said emitted light from said region to said photodetector means, (d) means coupled to the photodetector means for producing a signal corresponding to the difference in the output signals from the two photodetector means, and (e) means for displaying said difference signal.

15. The apparatus of claim 14 and wherein the means for directing the light to the region and transmitting light from the region comprises a fiber optic probe.

16. The apparatus of claim 15 and wherein each photo-detector means comprises a photodetector and a narrow band filter disposed in front of said photodetector.

17. The apparatus of claim 15 and wherein said light is mounted on said probe.

18. The apparatus of claim 15 and wherein said source of monochromatic light comprises a source of white light and a narrow band filter.

19. The apparatus of claim 14 and wherein said display is a buzzer.

20. The apparatus of claim 14 and wherein said display is a light.

21. The apparatus of claim 14 and wherein said display is a meter.

22. The apparatus of claim 14 and wherein said source of monochromatic light is a laser.

23. The apparatus of claim 14 and wherein said monochromatic light source is at a wavelength $\lambda_1$ and the photodetector means includes means for passing light at wavelength $\lambda_2$ and $\lambda_3$, wherein $\lambda_2$ is a wavelength where the intensity is about the same for caries and non-caries, $\lambda_3$ is a wavelength where the intensity changes in the presence of caries and $\lambda_1$ is a wavelength that will produce emission on teeth at $\lambda_2$ and $\lambda_3$.

24. The apparatus of claim 23 and wherein $\lambda_1$=around 410±5 nm, $\lambda_2$=between around 450 and 500 nm and $\lambda_3$=between around 540 and 620 nm.

25. A method for detecting the presence of caries in the teeth of a person comprising:

(a) exciting a region of the teeth to be examined with a beam of light that is at least substantially monochromatic at a wavelength [$\lambda_3$[ $\lambda_1$, (b) forming an image of the light emitted from the region at a wavelength $\lambda_3$ where the intensity [increases] *decreases* in the presence of caries, and (c) recording the image on a recording medium.

26. A method for detecting the presence of caries in the teeth of a person comprising:

(a) exciting a region of the teeth to be examined with a beam of substantially monochromatic light, said beam of monochromatic light having a wavelength $\lambda_1$, (b) measuring the intensity of the light emitted from the region at a wavelength $\lambda_3$, and (c) determining if caries is present in accordance with the intensity of the light emitted at the wavelength $\lambda_3$, wherein $\lambda_3$ is a wavelength where the intensity of emitted light [increases] *decreases* in the presence of caries and $\lambda_1$ is a wavelength which will produce emission from teeth at a wavelength $\lambda_3$.

27. The method of claim 26 and wherein $\lambda_1$ is a wavelength in the visible frequency range of the light spectrum.

28. Apparatus for use in detecting the presence of caries in the teeth of a person comprising:

(a) source means for generating a beam of monochromatic light having a wavelength $\lambda_1$, (b) means for directing light from said monochromatic source onto a region of teeth to be examined and receiving the light emitted therefrom, (c) means for measuring the intensity of the emitted light at a wavelength $\lambda_2$ and a wavelength $\lambda_3$, and (d) means for generating a signal related to $\lambda_2$ and $\lambda_3$, where $\lambda_2$ is a wavelength where the intensity is about the same for caries and noncaries, $\lambda_3$ is a wavelength where the intensity changes in the presence of caries and $\lambda_1$ is a wavelength that will produce emitted light when illuminating teeth at wavelengths $\lambda_2$ and $\lambda_3$.

*29. A method for detecting the presence of caries in the teeth of a person comprising:*

*radiating a region of the tooth to be examined with light;*

*selecting a first wavelength in the near neighborhood of a wavelength having a constant intensity of light from the tooth in caries and non-carious regions;*

*selecting a second wavelength where the intensity changes measurably from non-carious regions to caries;*

*producing first and second signals corresponding to the intensity of the light from the tooth at first and second wavelengths, respectively;*

*producing a third signal corresponding to the difference between said first and second signal;*

*adjusting the value of said third signal in a known non-carious region to a predetermined value;*

*detecting the presence of caries in other regions by said third signal changing from said predetermined value in a predetermined manner.*

*30. A method for detecting the presence of caries in the teeth of a person comprising:*

(a) *exciting a region of the teeth to be examined with a beam of light that is at least substantially monochromatic at a wavelength* $\lambda_1$;

(b) *forming an image of the light emitted from the region at a wavelength* $\lambda_3$ *where the intensity changes in the presence of caries; and*

(c) *recording the image on a recording medium.*

*31. A method for detecting the presence of caries in the teeth of a person comprising:*

(a) *exciting a region of the teeth to be examined with a beam of substantially monochromatic light, said beam of monochromatic light having a wavelength* $\lambda_1$;

(b) *measuring the intensity of the light emitted from the region at a wavelength* $\lambda_3$, *and*

(c) *determining if caries is present in accordance with the intensity of the light emitted at the wavelength* $\lambda_3$, *wherein* $\lambda_3$ *is a wavelength where the intensity of emitted light changes in the presence of caries and* $\lambda_1$ *is a wavelength which will produce emission from teeth at a wavelength* $\lambda_3$.

*32. The method of claim 31 and wherein* $\lambda_1$ *is a wavelength in the visible frequency range of the light spectrum.*

*33. A method for detecting the presence of caries in the teeth of a person as in claim 29 wherein said predetermined value is substantially zero.*

* * * * *